United States Patent [19]

Higashimura et al.

[11] Patent Number: 5,545,609
[45] Date of Patent: Aug. 13, 1996

[54] PESTICIDAL 3-PHENYLPYRAZOLE AQUEOUS SUSPENSION CONCENTRATE AND A PROCESS FOR PRODUCTION THEREOF

[75] Inventors: Minoru Higashimura, Ibaraki; Takashi Ootsuka, Tondabayashi; Masakazu Shibayama, Takatsuki, all of Japan

[73] Assignee: Nihon Nohyaku Co., Ltd., Tokyo, Japan

[21] Appl. No.: 319,028

[22] Filed: Oct. 6, 1994

[30] Foreign Application Priority Data

Oct. 12, 1993 [JP] Japan ................... 5-280081

[51] Int. Cl.$^6$ ........................ A01N 43/56
[52] U.S. Cl. ........................ 504/282
[58] Field of Search ........................ 504/282

[56] References Cited

U.S. PATENT DOCUMENTS

| | | | |
|---|---|---|---|
| 3,934,825 | 1/1976 | Delfosse et al. | 241/16 |
| 4,106,947 | 8/1978 | Recasens et al. | 106/57 |
| 4,663,364 | 5/1987 | Iwasaki et al. | 523/122 |
| 4,851,421 | 7/1989 | Iwasaki et al. | 514/352 |
| 5,032,165 | 7/1991 | Miura et al. | 71/92 |
| 5,112,384 | 5/1992 | Miura et al. | 71/92 |

FOREIGN PATENT DOCUMENTS

| | | |
|---|---|---|
| 103171 | 3/1984 | European Pat. Off. |
| 0443059 | 8/1991 | European Pat. Off. |
| 63-58802 | 11/1988 | Japan |
| 64-7041 | 2/1989 | Japan |
| 3-37483 | 6/1991 | Japan |
| 3-163063 | 7/1991 | Japan |
| 4-17923 | 3/1992 | Japan |
| 4-211065 | 8/1992 | Japan |

Primary Examiner—S. Mark Clardy

[57] ABSTRACT

A pesticidal aqueous suspension concentrate containing as an active ingredient a 3-substituted pyrazole derivative represented by the general formula (I):

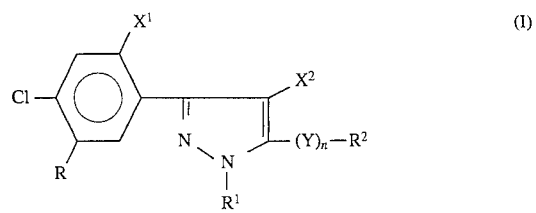

(wherein the substituents areas defined in the description of the specification)in which the 50% particle size and 90% particle size in cumulative particle size distribution of particles of the active ingredient are less than 1 μm and less than 2 μm, respectively, and which is harmless to useful crops and is equal to an emulsifiable concentrate in herbicidal effect; and a process for producing said pesticidal aqueous suspension concentrate.

2 Claims, No Drawings

PESTICIDAL 3-PHENYLPYRAZOLE AQUEOUS SUSPENSION CONCENTRATE AND A PROCESS FOR PRODUCTION THEREOF

BACKGROUND OF THE INVENTION

1. Field of the Invention

The present invention relates to a pesticidal aqueous suspension concentrate containing as an active ingredient a 3-substituted pyrazole derivative represented by the general formula (I):

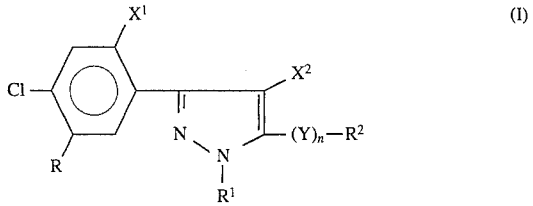

[wherein R is

—$Y^1R^3$ (wherein $R^3$ is a $C_1$-$C_6$ alkyl group, a $C_1$-$C_6$ haloalkyl group, a $C_2$-$C_6$ alkenyl group or a $C_2$-$C_6$ alkynyl group, and $Y^1$ is —O— or —S—),

—$Y^2CH(R^4)CO$—$OR^5$ (wherein $R^4$ is a hydrogen atom or a $C_1$-$C_6$ alkyl group, $R^5$ is a hydrogen atom, a $C_1$-$C_6$ alkyl group, a $C_1$-$C_6$ haloalkyl group, a $C_2$-$C_6$ alkenyl group or a $C_2$-$C_6$ alkynyl group, and $Y^2$ is —O—, —S— or —NH—).

—$COOCH(R^4)CO$—$Y^1R^5$ (wherein $R^4$, $R^5$ and $Y^1$ are as defined above), or

—$COOR^6$ (wherein $R^6$ is a $C_1$-$C_6$ alkyl group, a $C_1$-$C_6$ haloalkyl group, a $C_2$-$C_6$ alkenyl group or a $C_2$-$C_6$ alkynyl group), $R^1$ is a $C_1$-$C_6$ alkyl group, $R^2$ is a hydrogen atom, a $C_1$-$C_6$ alkyl group or a $C_1$-$C_6$ haloalkyl group, $X^1$ and $X^2$, which may be the same or different, are halogen atoms, Y is —O—, —S—, —SO— or —$SO_2$—, and n is zero or 1], the 50% particle size and 90% particle size in cumulative particle size distribution of particles of the active ingredient being 1 μm or less and 2 μm or less, respectively; and a process for producing said pesticidal aqueous suspension concentrate.

RELATED ART

The 3-substituted phenylpyrazole derivative of the general formula (I) is a compound described in Japanese Patent Unexamined Publication Nos. 3-163063 and 4-211065. As a herbicide, said derivative has an excellent herbicidal activity against all of herbaceous weeds which are harmful to upland farming. Particularly when applied for wheat (barley, oats or rye) cropping, said derivative exhibits a marked herbicidal effect on typical weeds such as cleavers (*Galium aparine*), chickweed (*Stellaria media*), birdseye speedwell (*Veronica persica*), sentless chamomile (*Matricaria inodora*), purple deadnettle (*Lamium purpureum*), henbit (*Lamium amplexicaule*), shepherd's purse (*Capsella bursapastoris*), marsh yelloweress (*Rorippa islandica*), sticky chickweed (*Cerastium viscosum*), common lambsquarters (*Chenopodium album*), tufted knotweed (*Polygonum longisetum*), prostrate knotweed (*Polygonum aviculare*), etc.

Post-emergence herbicides have been generally used in the form of emulsifiable concentrates, wettable powders, suspension concentrates, etc. In particular, the emulsifiable concentrates have a marked herbicidal effect.

However, blending of an organic solvent is indispensable for preparing the emulsifiable concentrate, so that the emulsifiable concentrates have defects such as undesirable effects on the environment and harmfulness to users. Moreover, the emulsifiable concentrates have a marked biological effect and hence are often not sufficient in selectivity between crops and weeds.

The wettable powders do not have the above defects of the emulsifiable concentrates but are generally often inferior to the emulsifiable concentrates in biological effect.

On the other hand, the suspensions are preparations which permit avoidance of the problems in the emulsifiable concentrates and the wettable powders. In recent years, many kinds of suspension concentrates have been developed.

The suspensions, however, are unavoidably inferior to the emulsifiable concentrates in biological effect, though not so much as the wettable powders. Particularly when a slightly water-soluble or water-insoluble active ingredient is used, the suspensions are markedly inferior to the emulsifiable concentrates in biological effect.

The 3-substituted phenylpyrazole derivative of the general formula (I) is very slightly water-soluble, and a conventional suspension concentrate containing active ingredient particles with average size above 1 μm thereof is markedly harmless to crops but has a biological effect lower than that of an emulsifiable concentrate, i.e., a suspension concentrate needs to apply at the dosage 4 to 8 times the dosage of emulsifiable concentrates.

As to these problems, it has been proposed that the biological effect of the suspensions should be improved by making an active ingredient into fine particles. For example, the following techniques have been proposed:

① a method in which the biological effect is improved by grinding an active ingredient finely to an average particle size of 0.5 μm or less by the use of grinding elements with diameter less than 0.5 mm (Japanese Patent Post-examined Publication Nos. 63-58802 and 64-7041), ② a method in which the improvement of the biological effect and the stabilization of dispersion in a diluent are achieved by grinding an active ingredient finely to adjust the product of the true specific gravity and the average particle size to 0.8 or less (Japanese Patent Post-examined Publication No. 3-37483), and ③ a method in which the reduction of phytotoxicity to broad-leaved crops and the enhancement of herbicidal effect are achieved by adjusting the particle size of 90% or more of an active ingredient to 5 μm or less and adjusting the average particle size to 0.3 to 3.0 μm (Japanese Patent Post-examined Publication No. 4-17923).

However, these methods make it possible to improve the biological effect by grinding an active ingredient finely, but they are very disadvantageous from the viewpoint of production efficiency, therefore commercial base production is impossible.

In detail, in the method ①, grinding for a long time of 3 to 12 hours by the use of glass beads with a diameter of 0.1 to 0.2 mm is necessary for obtaining fine particles with a predetermined particle size. Therefore, the production efficiency is very low and economical actual production is impossible.

In the method ②, grinding for a long time of 3 to 6 hours by the use of glass beads with a diameter of 1 mm is necessary as in the method ①. In the method ③, the time required for grinding is unknown, but glass beads with a diameter of 1 mm are used as in the method ②, so that grinding for a long period of time is necessary for attaining an average particle size of 1 μm or less.

Therefore, like the method ①, the methods ② and ③ are also not sufficient in production efficiency in actual production.

SUMMARY OF THE INVENTION

It is desired that a suspension containing a 3-substituted phenylpyrazole derivative of the general formula (I) as an active ingredient exhibits herbicidal effect equal to that of an emulsifiable concentrate while retaining harmlessness to useful crops. There is no conventional technique capable of solving this problem.

The present inventors earnestly investigated for solving this problem and consequently found that when active ingredient fine particles with a 50% particle size in cumulative particle size distribution of less than 1 μm and a 90% particle size in cumulative particle size distribution of less than 2 μm are obtained by wet fine grinding of a 3-substituted phenylpyrazole derivative of the general formula (I) by the use of hard grinding elements with density of larger than 4 g/cm³ and diameter of less than 1 mm and suspended in an aqueous medium to obtain an aqueous suspension concentrate, this composition exhibits herbicidal effect equal to an emulsifiable concentrate and has a reduced phytotoxicity to useful crops. Thus, the present invention has been accomplished. Hereinafter the 50% particle size in cumulative particle size distribution is sometimes referred to as a mean particle size.

DETAILED DESCRIPTION OF PREFERRED EMBODIMENTS

The 3-substituted phenylpyrazole derivative, i.e., the active ingredient used in the present invention is represented by the general formula (I) described below. Typical compounds as the 3-substituted phenylpyrazole derivative are listed in Table 1, but they are not intended in any way to limit the scope of the present invention.

General formula (I):

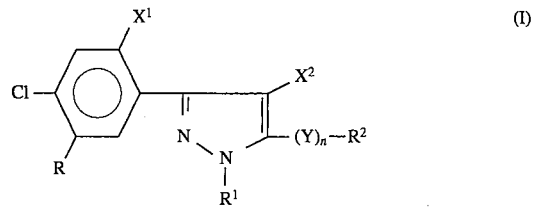

wherein R, R¹, R², X¹, X², Y and m are as defined above.

Of the substituents of the 3-substituted phenylpyrazole derivative of the general formula (I) used in the present invention, each alkyl group is a linear or branched alkyl group having 1 to 6 carbon atoms, each haloalkyl group is a substituted alkyl group having as the substituent(s) one or more halogen atoms which may be the same or different and are selected from the group consisting of chlorine, fluorine, iodine and bromine atoms, each lower alkenyl group is a linear or branched alkenyl group having 2 to 6 carbon atoms, and each alkynyl group is a linear or branched alkynyl group having 2 to 6 carbon atoms.

TABLE 1

| No | R | R² | X¹ | X² | (Y)n | Physical properties |
|---|---|---|---|---|---|---|
| | | ($R^1 = CH_3$) | | | | |
| 1 | $OCH_2CH=CH_2$ | $CH_3$ | Cl | Cl | S | nD 1.6131(25.3° C.) |
| 2 | $OCH_2CH=CH_2$ | $CHF_2$ | Cl | Cl | O | nD 1.5536(28.4° C.) |
| 3 | $OCH_2CH=CH_2$ | $CHF_2$ | F | Cl | O | m.p. 63.7–64.1° C. |
| 4 | $SCH_2CH=CH_2$ | $CH_3$ | Cl | Cl | S | paste |
| 5 | $SCH_2CH=CH_2$ | $CHF_2$ | Cl | Cl | O | m.p. 52.0–55.0° C. |
| 6 | $SCH_2CH=CH_2$ | $CHF_2$ | F | Cl | O | nD 1.5670(17.9° C.) |
| 7 | $OCH_2C\equiv CH$ | $CH_3$ | Cl | Cl | S | m.p. 71.5° C. |
| 8 | $OCH_2C\equiv CH$ | $CHF_2$ | Cl | Cl | O | m.p. 84.0° C. |
| 9 | $OCH_2C\equiv CH$ | $CHF_2$ | F | Cl | O | m.p. 98.0–98.1° C. |
| 10 | $SCH_2C\equiv CH$ | $CH_3$ | Cl | Cl | S | m.p. 94.5° C. |
| 11 | $SCH_2C\equiv CH$ | $CHF_2$ | Cl | Cl | O | m.p. 127–129° C. |
| 12 | $SCH_2C\equiv CH$ | $CHF_2$ | F | Cl | O | m.p. 82.8° C. |
| 13 | $OCH_2COOCH_3$ | $CH_3$ | Cl | Cl | S | m.p. 126.2° C. |
| 14 | $OCH_2COOCH_3$ | $CHF_2$ | Cl | Cl | O | m.p. 119.8° C. |
| 15 | $OCH_2COOCH_3$ | $CHF_2$ | Cl | Br | O | m.p. 133.8° C. |
| 16 | $OCH_2COOCH_3$ | $CHF_2$ | F | Cl | O | m.p. 122.8–123.1° C. |
| 17 | $OCH_2COOC_2H_5$ | $CH_3$ | Cl | Cl | S | m.p. 106.5° C. |
| 18 | $OCH_2COOC_2H_5$ | $CHF_2$ | Cl | Cl | O | m.p. 102.3° C. |
| 19 | $OCH_2COOC_2H_5$ | $CHF_2$ | F | Cl | O | m.p. 127.6° C. |
| 20 | $OCH_2COOC_3H_7\text{-}n$ | $CHF_2$ | Cl | Cl | O | m.p. 89.7° C. |
| 21 | $OCH_2COOC_3H_7\text{-}n$ | $CHF_2$ | F | Cl | O | m.p. 97.6–97.8° C. |
| 22 | $OCH_2COOC_3H_7\text{-}i$ | $CHF_2$ | Cl | Cl | O | m.p. 106.0° C. |
| 23 | $OCH_2COOC_3H_7\text{-}i$ | $CHF_2$ | F | Cl | O | m.p. 120.3–120.5° C. |
| 24 | $OCH_2COOCH_2CH=CH_2$ | $CHF_2$ | Cl | Cl | O | m.p. 84.7° C. |
| 25 | $OCH_2COOCH_2CH=CH_2$ | $CHF_2$ | F | Cl | O | m.p. 89.2–89.4° C. |
| 26 | $OCH_2COOCH_2C\equiv CH$ | $CHF_2$ | Cl | Cl | O | m.p. 119.6° C. |
| 27 | $OCH_2COOCH_2C\equiv CH$ | $CHF_2$ | F | Cl | O | m.p. 99.0° C. |
| 28 | $OCH(CH_3)COOH$ | $CH_3$ | Cl | Cl | S | m.p. 191–194° C. |
| 29 | $OCH(CH_3)COOCH_3$ | $CH_3$ | Cl | Cl | S | m.p. 90–93° C. |
| 30 | $OCH(CH_3)COOCH_3$ | $CHF_2$ | F | Cl | O | m.p. 95.6° C. |
| 31 | $OCH(CH_3)COOC_2H_5$ | $CH_3$ | Cl | Cl | S | nD 1.5763(28.8° C.) |
| 32 | $OCH(CH_3)COOC_2H_5$ | $CHF_2$ | Cl | Cl | O | nD 1.5238(25.7° C.) |

TABLE 1-continued (R¹ = CH₃)

| No | R | R² | X¹ | X² | (Y)n | Physical properties |
|---|---|---|---|---|---|---|
| 33 | OCH(CH₃)COOC₂H₅ | CHF₂ | Cl | Br | O | nD 1.5396(20.8° C.) |
| 34 | OCH(CH₃)COOC₂H₅ | CHF₂ | F | Cl | O | m.p. 67.0–67.2° C. |
| 35 | OCH(CH₃)COOC₃H₇-i | CH₃ | Cl | Cl | S | m.p. 87–90° C. |
| 36 | SCH(CH₃)COOCH₃ | CHF₂ | Cl | Cl | O | nD 1.5654(19.8° C.) |
| 37 | SCH(CH₃)COOCH₃ | CHF₂ | F | Cl | O | nD 1.5494(25.0° C.) |
| 38 | SCH(CH₃)COOC₂H₅ | CHF₂ | Cl | Cl | O | nD 1.5565(28.0° C.) |
| 39 | SCH(CH₃)COOC₂H₅ | CHF₂ | F | Cl | O | nD 1.5328(18.0° C.) |
| 40 | NHCH(CH₃)COOCH₃ | CH₃ | Cl | Cl | S | m.p. 144.2° C. |
| 41 | NHCH(CH₃)COOC₂H₅ | CH₃ | Cl | Cl | S | paste |
| 42 | NHCH(CH₃)COOC₂H₅ | CHF₂ | Cl | Cl | O | nD 1.5371(23.4° C.) |
| 43 | NHCH(CH₃)COOC₂H₅ | CHF₂ | F | Cl | O | nD 1.5264(26.6° C.) |
| 44 | COOCH₂COOCH₃ | CHF₂ | Cl | Cl | O | m.p. 74.4° C. |
| 45 | COOCH₂COOCH₃ | CHF₂ | F | Cl | O | nD 1.5350(27.3° C.) |
| 46 | COOCH₂COSCH₃ | CHF₂ | Cl | Cl | O | |
| 47 | COOCH₂COSCH₃ | CHF₂ | F | Cl | O | |
| 48 | COOCH₂COOC₂H₅ | CHF₂ | Cl | Cl | O | m.p. 57.2° C. |
| 49 | COOCH₂COOC₂H₅ | CHF₂ | F | Cl | O | nD 1.5362(23.4° C.) |
| 50 | COOCH₂COSC₂H₅ | CHF₂ | Cl | Cl | O | nD 1.5763(20.7° C.) |
| 51 | COOCH₂COSC₂H₅ | CHF₂ | F | Cl | O | nD 1.5536(27.3° C.) |
| 52 | COOCH₂COOC₃H₇-i | CHF₂ | Cl | Cl | O | nD 1.5289(24.0° C.) |
| 53 | COOCH₂COOC₃H₇-i | CHF₂ | F | Cl | O | |
| 54 | COOCH₂COSC₃H₇-i | CHF₂ | Cl | Cl | O | nD 1.5684(20.2° C.) |
| 55 | COOCH₂COSC₃H₇-i | CHF₂ | F | Cl | O | |
| 56 | COOCH₂COOCH₂CH=CH₂ | CHF₂ | Cl | Cl | O | m.p. 45.4° C. |
| 57 | COOCH₂COOCH₂CH=CH₂ | CHF₂ | F | Cl | O | |
| 58 | COOCH₂COOCH₂C≡CH | CHF₂ | Cl | Cl | O | m.p. 79.3° C. |
| 59 | COOCH₂COOCH₂C≡CH | CHF₂ | F | Cl | O | |
| 60 | COOCH(CH₃)COOCH₃ | CHF₂ | Cl | Cl | O | nD 1.5370(25.7° C.) |
| 61 | COOCH(CH₃)COOCH₃ | CHF₂ | F | Cl | O | nD 1.5314(23.0° C.) |
| 62 | COOCH(CH₃)COOC₂H₅ | CHF₂ | Cl | Cl | O | nD 1.5672(26.0° C.) |
| 63 | COOCH(CH₃)COOC₂H₅ | CHF₂ | F | Cl | O | nD 1.5212(14.1° C.) |
| 64 | COOCH₂C≡CH | CHF₂ | Cl | Cl | O | m.p. 78.5° C. |
| 65 | COOCH₃ | CHF₂ | Cl | Cl | O | m.p. 63.9° C. |
| 66 | COOCH₃ | CHF₂ | F | Cl | O | nD 1.5430(17.0° C.) |
| 67 | COOC₂H₅ | CH₃ | Cl | Cl | S | nD 1.6029(20.1° C.) |
| 68 | COOC₂H₅ | CHF₂ | Cl | Cl | O | nD 1.5446(26.8° C.) |
| 69 | COOC₂H₅ | CHF₂ | F | Cl | O | nD 1.5320(21.0° C.) |
| 70 | OCH₂CH=CH₂ | CHF₂ | Cl | Cl | NH | m.p. 80.6° C. |
| 71 | OCH₂C≡CH | CHF₂ | Cl | Cl | NH | m.p. 118.9° C. |
| 72 | OCH₂COOCH₃ | i-C₃H₇ | Cl | Cl | — | paste |
| 73 | OCH₂CH=CH₂ | i-C₃H₇ | Cl | Cl | — | paste |
| 74 | OCH₂C≡CH | i-C₃H₇ | Cl | Cl | — | paste |
| 75 | SCH₂COOCH₃ | t-C₄H₉ | Cl | Cl | — | paste |
| 76 | OCH₂CH=CH₂ | CH₂Br | Cl | Cl | — | paste |

The proportion of the active ingredient is reasonably chosen so that the active ingredient may not have phytotoxicity to crops to be protected by its application but may exhibit a sufficient herbicidal effect on weeds other than the crops. Usually, the proportion of the 3-substituted phenylpyrazole derivative of the general formula (I) may be properly chosen in the range of 0.1 to 20 parts by weight per 100 parts by weight of the pesticidal aqueous suspension concentrate.

The pesticidal aqueous suspension concentrate of the present invention can be produced by blending an aqueous medium with the above-mentioned fine particles obtained by grinding the active ingredient, a surfactant, a thickner and an antifreezing agent. If necessary, a stabilizer, an anti-foaming agent, an antiseptic, etc. may also be incorporated into the pesticidal aqueous suspension concentrate.

As the surfactant used in the present invention, there can be used, for example, anionic surfactants such as ligninsulfonates, alkylarylsulfonates, dialkyl sulfosuccinates, polyoxyalkylene alkyl aryl ether sulfates, alkylnaphthalene sulfonates, etc.; and nonionic surfactants such as polyoxyalkylene alkyl aryl ethers, polyoxyalkylene styryl phenyl ethers, polyoxyalkylene glycols, polyoxyalkylene alkyl ethers, polyoxyalkylene alkyl esters, etc. These surfactants may be used singly or as a mixture thereof.

The above-mentioned surfactant is necessary for carrying out wet fine grinding efficiently, and is effective in stabilizing the dispersion system of the resulting aqueous suspension concentrate. The proportion of the surfactant may be properly chosen in the range of 0.1 to 10 parts by weight per 100 parts by weight of the aqueous suspension concentrate.

As the thickner, there can be used, for example, natural polysaccharides such as xanthan gum, guar gum, gum arabic, alginic acid, etc.; inorganic viscous materials such as bentonite, etc.; semisynthetic viscous materials such as carboxymethyl cellulose, hydroxyethyl cellulose, etc.; and synthetic viscous materials such as poly(vinyl alcohol)s, poly(vinylpyrrolidone)s, carboxyvinyl polymers, etc. These thickners may be used singly or as a mixture thereof. The amount of the thickner used may be properly chosen in the range of 0.01 to 10 parts by weight.

The antifreezing agent is not particularly limited. For example, glycols such as ethylene glycol, propylene glycol, etc. can be used. The amount of the antifreezing agent used may be chosen in the range of 0 to 20 parts by weight.

As the grinding element for grinding the active ingredient finely to a mean particle size of less than 1 μm, any grinding element may be used so long as they have a density of larger than 4 g/cm³ and a diameter of less than 1 mm. For example, grinding element such as ceramic beads, high-purity $ZrO_2$ beads, etc. can be used.

The density of the grinding element affects the grinding efficiency greatly. The density of generally used glass beads is 3 g/cm$^3$ or less and is not sufficiently different from that of a material to be ground, so that the grinding efficiency is low, resulting in a very long grinding time. When grinding element with diameter of larger than 1 mm are used, spaces among them are wide, so that fine grinding to a mean particle size of less than 1 μm is impossible.

The wet fine grinding can be carried out with a conventional mill, without any special conditions except for using the above-exemplified rigid media.

Pre-grinding of the active ingredient is effective in improving the efficiency of the fine grinding, though the extent depends on physical properties of the material to be ground (the active ingredient).

EXAMPLES

Typical examples, comparative examples and test examples of the present invention are described below but they should not be construed as limiting the scope of the invention.

In the examples and the comparative examples, parts are all by weight.

Example 1

3.0 Parts of dioctyl sulfosuccinate, 6.0 parts of a polyoxyethylene phenyl alkylaryl ether sulfate, 10.0 parts of propylene glycol, 0.1 part of benzoisothiazoline and 0.5 part of silicone emulsion were mixed with 77.5 parts of water to effect dissolution. Then, 2.5 parts of compound No. 19 dry-ground to an average particle size of 21 μm was dispersed in and mixed with the resulting mixture.

The mixture thus obtained by the dispersion was charged into a DYNO-MILL Model KDL (mfd. by Bachofen Co., Ltd.) equipped with a vessel with a capacity of 350 ml, together with 280 ml of ceramic beads with a particle size of 0.3 mm and a density of 6 g/cm$^3$ (TORAYCERAM, mfd. by Toray Industries, Inc.), and subjected to wet grinding at a revolution rate of an agitator of 2,000 rpm. Samples were collected at predetermined intervals as samples for measuring the change of the particle size with the lapse of time.

Example 2

Wet grinding was carried out in the same manner as in Example 1 except for changing the particle size of the ceramic beads to 0.6 mm. Samples were collected at predetermined intervals as samples for measuring the change of the particle size with the lapse of time.

Example 3

With 99.6 parts of a suspension obtained by wet grinding for 30 minutes in the same manner as in Example 1 was uniformly mixed 0.4 parts of xanthan gum to obtain a suspension concentrate of compound No. 19 having a mean particle size of 0.3 μm.

Comparative Example 1

Wet grinding was carried out in the same manner as in Example 1 except for using glass beads with a particle size of 0.3 mm and a density of 2.3 g/cm$^3$ in place of the ceramic beads. Samples were collected at predetermined intervals as samples for measuring the change of the particle size with the lapse of time.

Comparative Example 2

With 99.6 parts of a suspension obtained by wet grinding for 150 minutes in the same manner as in Comparative Example 1 was uniformly mixed 0.4 parts of xanthan gum to obtain a suspension concentrate of compound No. 19 having a mean particle size of 3.3 μm.

Comparative Example 3

2.5 Grams of compound No. 19, 10 parts of N-methyl-2-pyrrolidone, 80 parts of solvesso 200 (mfd. by Exxon Chemical Co., Ltd.) and 10 parts of SP-3005X (mfd. by TOHO KAGAKU K.K.) were mixed to effect dissolution, whereby an emulsifiable concentrate containing 2.5% of compound No. 19 was obtained.

Test Example 1

The particle size of the active ingredient of each of the samples collected in Examples 1 and 2 was measured by means of a laser granulometer (LPA-3000, mfd. by OTSUKA ELECTRONICS CO., LTD.) and a Coulter counter type granulometer (ELZONE particle counter, mfd. by Particle Data Co., Ltd.).

For comparison, the particle size of the active ingredient of each of the samples collected in Comparative Example 1 was measured in the same manner as above.

The results obtained are shown in Table 2.

TABLE 2

| Grinding time | Example 1 (μm) | | Example 2 (μm) | | Comparative Example 1 (μm) | |
| --- | --- | --- | --- | --- | --- | --- |
| (min.) | 50% | 90% | 50% | 90% | 50% | 90% |
| 0 | 21.0 | — | 21.0 | — | 21.0 | — |
| 10 | 1.0 | 5.2 | 3.0 | 7.8 | 10.5 | 18.5 |
| 20 | 0.5 | 1.3 | 1.0 | 3.5 | 7.6 | 15.3 |
| 30 | 0.3 | 0.8 | 0.5 | 1.0 | 7.3 | 14.7 |
| 40 | 0.3 | 0.8 | 0.4 | 0.9 | 6.6 | 12.8 |
| 50 | 0.2 | 0.7 | 0.3 | 0.7 | 6.0 | 12.0 |
| 60 | 0.2 | 0.6 | 0.2 | 0.7 | 5.5 | 12.0 |
| 90 | 0.15 | 0.6 | 0.2 | 0.6 | 4.7 | 12.4 |
| 120 | 0.15 | 0.6 | 0.15 | 0.6 | 4.3 | 12.1 |
| 150 | 0.15 | 0.6 | 0.15 | 0.6 | 3.3 | 10.6 |
| 180 | 0.15 | 0.6 | 0.15 | 0.7 | 2.0 | 9.7 |
| 240 | 0.15 | 0.6 | 0.15 | 0.7 | 1.5 | 8.2 |

As shown in Table 2, the time required for the particle size and 90% particle size in cumulative particle size distribution of particles of the active ingredient to be reduced to less than 1 μm and less than 2 μm, respectively, by wet fine grinding is 20 minutes in Example 1 and 30 minutes in Example 2. On the other hand, it is clear that in Comparative Example 1, the active ingredient are not ground to particle sizes in the above ranges even by grinding for 240 minutes.

Test Example 2

A plastic pot with a diameter of 12 cm and a height of 12 cm was filled with sifted upland soil and seeded with wheat, cleavers (*Galium aparine*) and birdseye speedwell (*Veronica persica*) so as to adjust the depth of covering soil to 1 cm, and these plants were grown in a greenhouse.

When the wheat was grown to a leaf stage of 3 and the cleavers and birdseye Speedwell were grown to a leaf stage of 1, a spray mix containing a predetermined concentration of each of the preparations obtained in Example 3 and Comparative Examples 2 and 3 was sprayed uniformly on the stalk and leaves in a spray volume of 300 liters per hectare by the use of a laboratory sprayer.

After being treated with the preparation, the plants were grown in the greenhouse for 14 days and the phytotoxicity to wheat and the herbicidal effect on the weeds were visually judged in the range of zero (no phytotoxicity or no herbicidal effect) to 100 (complete kill).

The results obtained are shown in Table 3.

TABLE 3

| Preparation | Dosage (g/ha) | Phyto- toxicity Wheat | Herbicidal activity Cleavers | Birdseye speedwell |
|---|---|---|---|---|
| Example 3 | 5 | 0 | 100 | 100 |
|  | 10 | 0 | 100 | 100 |
| Comparative Example 2 | 5 | 0 | 50 | 10 |
|  | 10 | 0 | 97 | 90 |
| Comparative Example 3 | 5 | 0 | 100 | 100 |
|  | 10 | 8 | 100 | 100 |

As shown in Table 3, the aqueous suspension concentrate of the present invention does not have phytotoxicity to wheat but has a marked herbicidal effect on harmful weeds. Its herbicidal effect is the same as that of an emulsifiable concentrate.

What is claimed is:

1. A pesticidal composition in concentrate aqueous suspension containing as an active ingredient 3-substituted pyrazole derivative represented by the general formula (I):

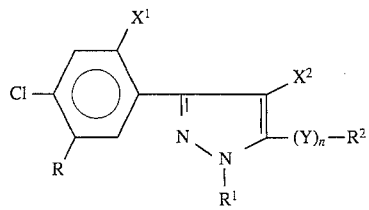

wherein R is

—$Y^1R^3$ (wherein $R^3$ is a $C_1$-$C_6$ alkyl group, a $C_1$-$C_6$ haloalkyl group, a $C_2$-$C_6$ alkenyl group or a $C_2$-$C_6$ alkynyl group, and $Y^1$ is —O— or —S—),

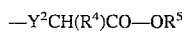
—$Y^2CH(R^4)CO$—$OR^5$ (wherein $R^4$ is a hydrogen atom or a $C_1$-$C_6$ alkyl group, $R^5$ is a hydrogen atom, a $C_1$-$C_6$ alkyl group, a $C_1$-$C_6$ haloalkyl group, a $C_2$-$C_6$ alkenyl group or a $C_2$a-$C_6$ alkynyl group, and $Y^2$ is —O—, —S— or —NH—),

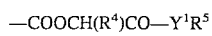
—COOCH($R^4$)CO—$Y^1R^5$ (wherein $R^4$, $R^5$ and $Y^1$ are as defined above), or

—$COOR^6$ (wherein $R^6$ is a $C_1$-$C_6$ alkyl group, a $C_1$-$C_6$ haloalkyl group, a $C_2$-$C_6$ alkenyl group or a $C_2$-$C_6$ alkynyl group), $R^1$ is a $C_1$-$C_6$ alkyl group, $R^2$ is a hydrogen atom, a $C_1$-$C_6$ alkyl group or a $C_1$-$C_6$ haloalkyl group, $X^1$ and $X^2$, which may be the same or different, are halogen atoms, Y is —O—, —S—, —SO— or —$SO_2$—, and n is zero or 1, said composition comprising said active ingredient in particulate form wherein 90% of the particles are less than 2 μm in diameter, with 50% of the particles less than 1 μm in diameter; and said particles being obtained by subjecting said active ingredient to a grinding step employing a hard grinding element having a density of larger than 4 g/cm³ and a particle size of less than 1 mm.

2. A process for producing a pesticidal composition in concentrate aqueous suspension containing as an active ingredient a 3-substituted pyrazole derivative represented by the general formula (I):

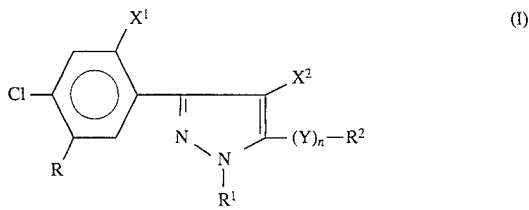

wherein R is

—$Y^1R^3$ (wherein $R^3$ is a $C_1$-$C_6$ alkyl group, a $C_1$-$C_6$ haloalkyl group, a $C_2$-$C_6$ alkenyl group or a $C_2$-$C_6$ alkynyl group, and $Y^1$ is —O— or —S—),

—$Y^2CH(R^4)CO$—$OR^5$ (wherein $R^4$ is a hydrogen atom or a $C_1$-$C_6$ alkyl group, $R^5$ is a hydrogen atom, a $C_1$-$C_6$ alkyl group, a $C_1$-$C_6$ haloalkyl group, a $C_2$-$C_6$ alkenyl group or a $C_2$,-$C_6$ alkynyl group, and $Y^2$ is —O—, —S— or —NH—),

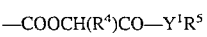
—COOCH($R^4$)CO—$Y^1R^5$ (wherein $R^4$, $R^5$ and $Y^1$ are as defined above), or

—$COOR^6$ (wherein $R^6$ is a $C_1$-$C_6$ alkyl group, a $C_1$-$C_6$ haloalkyl group, a $C_2$-$C_6$ alkenyl group or a $C_2$-$C_6$ alkynyl group), $R^1$ is a $C_1$-$C_6$ alkyl group, $R^2$ is a hydrogen atom, a $C_1$-$C_6$ alkyl group or a $C_1$-$C_6$ haloalkyl group, $X^1$ and $X^2$ which may be the same or different, are halogen atoms, Y is —O—, —S—, —SO— or —$SO_2$—, and n is zero or 1, said process comprising the steps of:

subjecting the active ingredient to wet fine grinding by the use of hard grinding element with a density of larger than 4 g/cm³ and resulting in particles wherein 90% of the particles are less than 2 μm in diameter, with 50% of the particles less than 1 μm in diameter.

* * * * *